US008404225B2

(12) United States Patent
Silk et al.

(10) Patent No.: US 8,404,225 B2
(45) Date of Patent: Mar. 26, 2013

(54) **CONTACT SEX PHEROMONE COMPONENT OF THE EMERALD ASH BORER *AGRILUS PLANIPENNIS* FAIRMAIRE (COLEOPTERA: BUPRESTIDAE)**

(75) Inventors: Peter Silk, Fredericton (CA); Jon Sweeney, New Maryland (CA); Krista Ryall, Sault Ste. Marie (CA); Barry Lyons, Hilton Beach (CA)

(73) Assignee: National Research Council of Canada, Ottawa, Ontario (CA)

( * ) Notice: Subject to any disclaimer, the term of this patent is extended or adjusted under 35 U.S.C. 154(b) by 378 days.

(21) Appl. No.: 12/591,535

(22) Filed: Nov. 23, 2009

(65) Prior Publication Data
US 2010/0143429 A1    Jun. 10, 2010

Related U.S. Application Data

(60) Provisional application No. 61/193,384, filed on Nov. 21, 2008.

(51) Int. Cl.
*A01N 25/08* (2006.01)
*A01N 25/32* (2006.01)
*A01N 27/00* (2006.01)
*A01N 65/00* (2009.01)

(52) U.S. Cl. .......... 424/84; 424/406; 424/409; 424/771; 514/762

(58) Field of Classification Search ................ None
See application file for complete search history.

(56) References Cited

PUBLICATIONS

Ginzel MD, Blomquist GJ, Millar JG, Hanks LM (2003b) Role of contact pheromones in mate recognition in *Xylotrechus colonus*. J Chem Ecol 29:533-545.

Haack RA, Jendek E, Liu K, Marchant TR, Petrice TR, Poland TM, Ye H (2002) The emerald ash borer: a new exotic pest in North America. Newslett Mich Entomol Soc 47:1-5.
Otis GW, Youngs ME, Umphrey G (2005) Effects of colored objects and purple background on emerald ash borer trapping. In: Mastro V, Reardon R (eds) Emerald Ash Borer Research and Technology Development Meeting. USDA, Forest Health Technology Enterprise Team, Morgantown, WV, pp. 31-32.
Rodriguez-Saona, C, Poland TM, Miller JR, Stelinski LL, Grant GG, de Groot P, Buchan L, MacDonald L (2006) Behavioural and electrophysiological responses of the emerald ash borer, *Agrilus planipennis*, to induced volatiles of Manchurian Ash, *Fraxinus mandshurica*. Chemoecology 16:75-86.

(Continued)

*Primary Examiner* — Neil Levy
(74) *Attorney, Agent, or Firm* — Sonia Patenaude

(57) ABSTRACT

The invention disclosed relates to the detection of the Emerald Ash Borer (EAB), *Agrilus planipennis* Fairmaire (Coleoptra: *B-prestidae*) and in particular to the use of contact sex phenomones therefor. Analysis of the elytral hydrocarbons from male and female emerald ash borer, that were freshly emerged vs. sexually mature (>10 days old) revealed a female-specific compound, 9-methyl-pentacosane (9-Me-$C_{25}$), only present in sexually mature females. This material was synthesized by the Wittig reaction of 2-decanone with (n-hexadecyl)-triphenylphosphonium bromide followed by catalytic reduction to yield racemic 9-Me $C_{25}$, which matched the natural compound by GC/MS (retention time and EI-mass spectrum). In field bioassays with freeze-killed sexually mature *A. planipennis* females, feral males spent significantly more time in contact and attempting copulation with unwashed females than with females that had been washed in n-hexane to remove the cuticular hydrocarbons. Hexane-washed females to which 9-Me-$C_{25}$ had been reapplied elicited similar contact time and percentage of time attempting copulation as unwashed females, indicating that 9-methyl-pentacosane is a contact sex-pheromone component of *A. planipennis*. This is the first contact sex pheromone identified in the Buprestidae.

4 Claims, 2 Drawing Sheets

PUBLICATIONS

Lelito JP, Frazer I, Mastro V, Tumlinson JH, Böröczky K, Baker TC (2007) Visually mediated 'paratrooper copulations' in the mating behaviour of *Agrilus planipennis* (Coleoptera: Buprestidae), a highly destructive invasive pest of North American ash trees. J Insect Behav 20:537-552.

Lelito JP, Frazer I, Mastro V, Tumlinson JH, Baker TC (2008) Novel visual-cue-based sticky traps for monitoring of emerald ash borers, *Agrilus planipennis*, J Appl Entomol 132:668-674.

Francese JA, Mastro VC, Oliver JB, Lance DR, Youseff N, Lavalee SG (2005) Evaluation of colors for trapping *Agrilus planipennis* (Coleoptera: Buprestidae). J Entomol Sci 40:93-95.

Crook DJ, Krimian A, Francese J, Fraser I, Poland TM, Sawyer AJ, Mastro V (2008) Development of a host-based semiochemical lure for trapping emerald ash borer *Agrilus planipennis* (Coleoptera: Buprestidae). Environ Entomol 37:356-365.

de Groot P, Grant GG, Poland TM, Scharbach R, Buchan L, Nott RW, Macdonald L, Pitt D (2008) Electrophysiological response and attraction of emerald ash borer to green leaf volatiles (GLVs) emitted by host foliage. J Chem Ecol 34:1170-1179.

Bartelt R, Cosse AA, Zilkowski BW, Fraser I (2007) Antennally active macrolide from the emerald ash borer *Agrilus planipennis* emitted predominantly by females. J Chem Ecol 33:1299-1302.

Dunn JP, Potter DA (1988) Evidence for sexual attraction by the twolined chestnut borer, *Agrilus bilineatus* (Weber) (Coleoptera: Buprestidae). Can Entomol 120:1037-1039.

Nelson DR, Blomquist GJ (1995) Insect waxes. In: Hamilton RJ (ed) Waxes: chemistry, molecular biology and functions. Oily Press, Dundee, Scotland, pp. 1-90.

CONTACT SEX PHEROMONE COMPONENT OF THE EMERALD ASH BORER *AGRILUS PLANIPENNIS* FAIRMAIRE (COLEOPTERA: BUPRESTIDAE)

PRIOR APPLICATION INFORMATION

This application claims the benefit of U.S. Provisional application Ser. No. 61/193,384, filed 21 Nov. 2008.

BACKGROUND OF THE INVENTION

This invention relates to the detection of wood boring insects, and in particular to the use of contact sex pheromones in the detection and identification of the Emerald Ash Borer (EAB) *Agrilus planipennis* Fairmaire (Coleoptra: Buprestidae).

The waxy layer on the cuticle of insects provides a hydrophobic barrier that prevents desiccation and may also provide patterns for mimicry or camouflage, repel excess rainwater, reflect solar radiation, and give species-specific olfactory cues. Some of the hydrocarbon components also function as contact pheromones. There is good evidence that in the Cerambycidae, mate recognition is mediated by contact chemoreception with this waxy layer wherein males orient to females only after antennal contact with the cuticle of a female (live or freeze-killed) with subsequent copulatory behavior and coupling to the females' genitalia (Ginzel et al. 2003[1]). The reference also discloses a female cuticular hydrocarbon extract containing 9-methylpentacosane, as a contact pheromone for *Xylotrehus colanus* (Coleoptra: Cerambycidae). Whether or not contact chemoreception is important in the Buprestidae such as the EAB, is unknown.

The emerald ash borer (EAB), *Agrilus planipennis* Fairmaire (Coleoptera: Buprestidae), is an invasive buprestid species originating from Asia that has caused extensive mortality of ash trees (*Fraxinus* spp. L.) (Oleaceae) since its introduction into the USA and Canada (Haack et al. 2002[2];) and its continued spread in North America threatens all native ash species. Movement of infested firewood and nursery stock has exacerbated the natural spread of EAB and large-scale devastation of ash trees has occurred in both urban and rural environments. Monitoring of this rapid spread has proven challenging because it is very difficult to detect low to moderate densities of EAB using visual surveys, and evidence to date suggests that EAB use visual cues rather than pheromones to locate mates (Otis et al. 2005[3]; Rodriguez-Soana et al. 2006[4]; Lelito et al. 2007[5], 2008[6]). Trap trees, consisting of girdled ash trees with sticky bands, have detected new outlier EAB infestations but they are labor intensive. Purple-colored sticky traps catch EAB better than any other color tested (Francese et al. 2005[7]), particularly when these traps are baited with host volatiles, either sesquiterpenes found in ash bark (Crook et al. 2008[8]) or ash leaf volatiles (Rodriguez-Soana et al. 2006[4]; de Groot et al. 2008[9]). Although an antennally active compound emitted primarily by female EAB has been identified (Bartelt et al. 2007[10]), its biological activity has yet to be demonstrated. Improved detection methods and management tools are urgently required but there is a paucity of information on the chemical ecology of this insect.

The mating biology of the EAB is poorly understood. For other buprestids, it has been suggested that individuals locate a susceptible host and then search for mates using visual and tactile cues. (Dunn and Potter 1988[11]) observed greater catches of male twolined chestnut borer, *Agrilus bilineatus* (Weber), in cages containing conspecific females than in empty cages, and suggested the attraction could be due either to a pheromone or to auditory cues produced by the females. Visual cues have clearly been demonstrated to be important in orienting EAB males to potential mates (Otis et al. 2005[3]; Lelito et al. 2007[5], 2008[6]). Dead EAB adults of either sex, whether they had been washed in solvent or not, elicited the same number of approaches by feral male EAB; in addition, males spent comparatively more time investigating unwashed females than males or washed females, suggesting the presence of a contact pheromone on the cuticle of female EAB (Lelito et al. 2007[5]). The identity or chemical composition of this putative contact pheromone was not determined.

Information on the identity and biological activity of an EAB contact pheromone would increase our understanding of the mating ecology of this and other buprestid species.

SUMMARY OF THE INVENTION

According to the invention, we now provide the isolation, identification, synthesis and biological activity of a sexually mature female-produced contact sex pheromone for the Emerald Ash Borer (EAB). *Agrilus planipennis* Fairmaire (Coleoptra: Buprestidae). The phenomone has been identified as 9-methyl pentacosane (9-MeC$_{25}$).

According to one aspect of the invention, a composition is provided for the attraction and detection of a sexually mature male Emerald Ash Borer (EAB) *Agrilus planipennis* Fairmaire (Coleoptra: Buprestidae), comprising a substrate and applied to the substrate, an attracting effective amount of 9-methyl pentacosane.

It is contemplated that the 9-methyl pentacosane may be in the racemic form, including its two S- and R-chiral enantiomers, or in a pure R- or S-form showing the requisite activity.

It is also contemplated that the active compound can be presented in combination with host plant volatiles, e.g. either sesquiterpenes found in ash bark (Crook et al. 2008[8]) or ash leaf volatiles (Rodriguez-Soana et al. 2006[4]; de Groot et al. 2008[9]), the Disclosures of which are Incorporated herein by Reference.

According to another aspect of the invention, we also provide a method for the attraction and detection of the emerald ash borer *Agrilus planipennis* (Coleoptra: Buprestidae), by applying to a substrate, an attracting effective amount of 9-methyl pentacosane. For example, the substrate can be a dead female or likeness thereof, located in an insect habitat.

It will be appreciated that having attracted the EAB in this manner, an insecticide and or an insect trap including the baited substrate, could be included to eradicate and/or capture the insects.

According to another aspect of the invention, a process is provided for making racemic 9-methyl pentacosane (9-MeC$_{25}$), a racemic mixture of the 9R- and 9S-enantiomers, comprising (a) the base-catalyzed Wittig coupling of 2-decanone with (n-hexadecyl)triphenylphosphonium bromide to form an alkene, and (b) concomitant catalysed hydrogenation of the resultant alkene, using a noble metal catalyst e.g Pd/C.

According to another aspect of the invention, a process is provided for making pure (S)-9-methylpentacosane(9-MeC$_{25}$), comprising (a) alkylating (R)-citronellyl bromide with the Grignard reagent n-hexylmagnesium bromide in the presence of lithium tetrachlorocuprate as catalyst to form an alkene, (b) ozonloysis of the alkene followed by reductive workup with triphenylphosphine, (c) a Wittig reaction of the compound so formed with tridecyltriphenyl phosphonium bromide and n-butyllithium to form a mixture of cis and trans alkenes, and (d) hydrogenation thereof under a noble metal catalyst e.g. Pd/C, to form (S)-9-methylpentacosane (9-MeC$_{25}$).

According to yet another aspect of the invention, a process is provided for making pure (R)-9-methylpentacosane(9-MeC$_{25}$), comprising (a) alkylating (S)-citronellyl bromide with the Grignard reagent n-hexylmagnesium bromide in the presence of lithium tetrachlorocuprate as catalyst to form an alkene, (b) ozonloysis of the alkene followed by reductive workup with triphenylphosphine, (c) a Wittig reaction of the compound so formed with tridecyltriphenyl phosphonium bromide and n-butyllithium to form a mixture of cis and trans alkenes, and (d) hydrogenation thereof under a noble metal catalyst e.g. Pd/C, to form (S)-9-methylpentacosane (9-MeC$_{25}$).

BRIEF DESCRIPTION OF THE DRAWINGS

FIG. 1(c) is the EI mass spectrum of 9-Me-C$_{25}$ found on 14-day-old females. Analysis conditions are described in the text. Numbers on peaks refer to compounds in Table 1; x=solvent impurity.

DETAILED DESCRIPTION OF THE INVENTION

Figure 1:
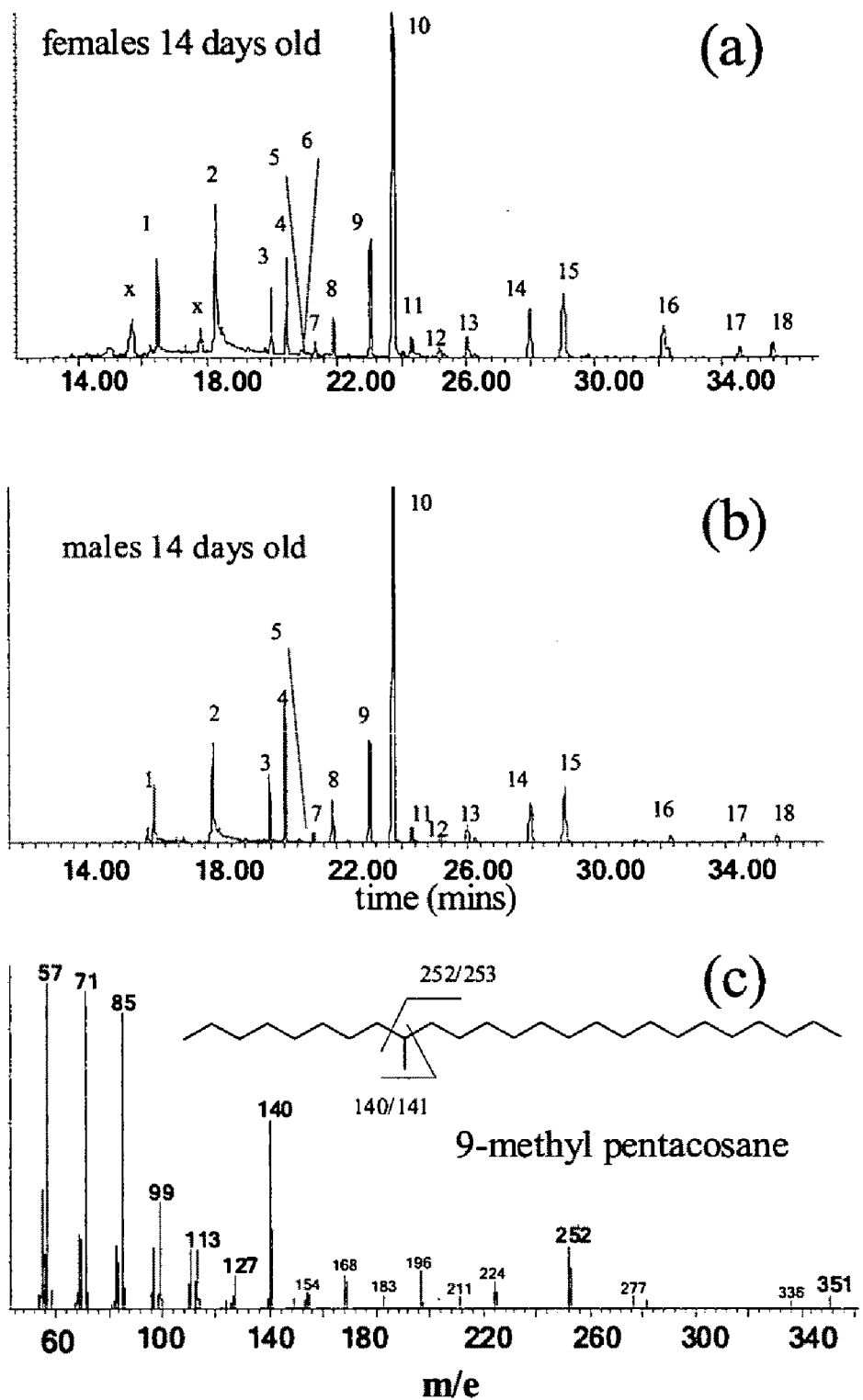
FIG. 1. Are graphs illustrating the SPME analysis of the cuticular hydrocarbons from the elytra of 14-day-old female (a) and male (b) emerald ash borer.

Materials and Methods
Source of Beetles

Trees infested with overwintering larvae of EAB were located in Windsor and Toronto, Ontario, felled, cut into bolts, transported in secure containers to the Great Lakes Forestry Centre in Sault Ste. Marie, Ontario, and placed into cold storage in a secure quarantine facility. As required, bolts were removed from cold storage and placed in rearing cages housed at 24° C. and a 16:8 h light:dark (L:D) photoperiod. Upon emergence, adult insects were separated by sex. A subset of males and females were frozen on the day of emergence and the rest were reared for 14 days to produce sexually mature adults before being frozen. Previous studies have demonstrated that mating only occurs in EAB once females are a minimum of 5-7 days from eclosion. All adults were maintained for 10-14 days at about 21° C., 50% relative humidity (RH) and a 16:8 h L:D cycle and were supplied with water and fresh foliage of evergreen ash, *Fraxinus uhdei* (Wenzig) Lingelsh, or green ash, *Fraxinus pennsylvanica* Marsh.

Identification of Cuticular Hydrocarbons

The relative abundances of cuticular hydrocarbons were determined using a manual solid-phase microextraction (SPME) assembly with a red 100-μm polydimethylsiloxane fibre (Supelco, PA). Insects were held with forceps and the fibre wiped across the elytra for about 30 seconds while rotating but not bending it. For each sex and maturity class (i.e., 1-day-old males, 1-day-old females, 10- to 14-day-old males, 10- to 14-day-old females), a minimum of six individuals were sampled and analyzed as composites.

The SPME samples and solvent extracts were analyzed by gas chromatography/mass spectrometry (GC/MS) on a Hewlett-Packard 5890 GC and a 5971 mass selective detector in the electron impact (EI, 70 eV) mode. The column used for analysis was a Supelco SPB-5 capillary (30 m×0.32 mm×0.25 μm film) in the splitless mode with helium as carrier gas. The injection port was at 280° C. for solvent extracts and 250° C. for SPME fibres. The oven temperature was programmed from 70° C., held for 1 min and then increased at 10° C./min to 240° C. and held for 30 min. Hydrocarbons were identified by comparing mass spectra and retention times with those of synthetic standards with reference to the parent M$^+$ and molecular formulae. Diagnostic mass spectral fragments unequivocally demonstrated the position of methyl branches Synthesis of Racemic 9-Methyl Pentacosane Synthetic racemic 9-methyl pentacosane (9-methyl-C$_{25}$), a racemic mixture of the 9R- and 9S-enantiomers, was prepared from base-catalyzed Wittig coupling of 2-decanone with (n-hexadecyl)triphenylphosphonium bromide and concomitant Pd/C hydrogenation of the resultant alkene. All other methyl-branched compounds (see Table 1) were synthesized in a similar manner. N-alkanes were obtained from Sigma Aldrich (Oakville, ON, Canada) or Alltech (Deerfield, Ill., USA).

Field Bioassays

Preparation of dummy females. A total of 78 EAB females that emerged from 10-15 Jul. 2008 were reared for the field bioassay. Female EAB were reared in the quarantine facilities, as described above, until the age of 14 days, when they were frozen. Prior to the field bioassay, females were removed from the freezer and thawed for 2-3 h. For 52 of the females, each female was individually rinsed in 1 ml of hexane for about 2 min. Females were then allowed to dry for a minimum of 30 min before being rinsed again. Females were rinsed a total of three times for 2 min each time and left to dry overnight after the final rinsing. All 78 females were then individually pinned through the right elytra at its base; the heads of the pins were then snipped off such that the end of the pin was only about 1 mm above the surface of the female's body and thus would not interfere with approaches by feral male EAB. Twenty-six of the rinsed females were then treated with 1 μl of racemic 9-methyl pentacosane (ca. 5 mg/ml; one female equivalent), in solution with hexane, and allowed to dry. This divided the 78 females into three treatment groups (unwashed, washed, and washed then treated). The treatment groups were indicated by pinning a small paper insect 'point' underneath the female that was not visible from above. The points were colored white (unwashed), yellow (washed) or blue (washed then treated). The paper points were shorter and narrower than the females' abdomen, were not visible from above, and did not appear to influence the behavior of the wild males. Females were kept at 3-4° C. in a fridge for 2 days until used in the bioassay and were transported to the field in a cooler.

Behavioral field bioassay. The field bioassay was conducted from 7-11 Jul. 2008 at a site about 1.8 km northeast of Port Lambton, ON (42° 40.16' N, 82° 29.56' W). Observations of feral males were made between 1000 and 1830 EDT, based on reports of EAB's most active time of day (Lelito et al. 2007[5]) About 40 h were spent observing feral males and collecting data on mating behavior. Dummy females were pinned to foliage on epicormic shoots of infested ash trees, growing from the base of the tree up to about 1.5 m above the ground. Females were placed and removed from foliage by grasping the pin underneath the female with tweezers and were never touched directly to avoid cross-contamination. Trees were chosen based on the presence of both epicormic shoots and feral EAB males on the foliage. Dummy females were placed in a triangle shape in groups of three (one of each treatment) about 20-30 cm apart. All females were pinned on south-facing foliage so that they would be in direct sunlight. From nine to 21 females were set up at different times on different trees, based on the amount of foliage available.

Observations of dummy females began once all females were established on the foliage, and lasted for about 1 h per observation session with breaks of 5-10 min in between observation sessions. We recorded the time of arrival of each male observed to land on a female and then the time of departure for that same male to obtain its total time spent in contact with a given female. The locations of the various treatments were not recorded, so the observations on time spent in contact by males was collected by observers who were unaware of the treatment. The treatment group (un-washed, treated, washed) was then recorded by checking for the presence of the colored insect point under the female's abdomen after the male had flown away. For a subset of males that spent several minutes or more in contact with a given female (n=7, 7, and 10 for unwashed, washed and treated, and washed-only females, respectively), we were able to record approximately every minute whether the male was attempting to mate with the female or whether he was merely in contact with her; from this, we were able to calculate the percentage of time spent attempting to mate vs. time spent simply in contact with the females.

The amount of time individual males spent in contact, and the percentage of that time spent attempting to mate, with females of the three different treatments were analyzed by one-way ANOVA after logarithmic transformation of data to meet the assumptions of normality of data and equality of variance; means were compared using the Holm-Sidak test. All analyses were conducted using SigmaStat (Vers. 3.5).
Results
GC/MS Analyses Analysis of SPME samples from the cuticle of EAB revealed no differences in the hydrocarbon profiles of males and females that were 1 day old (i.e., sexually immature) or between 1-day-old and 10- to 14-day-old males, but one compound was present exclusively in 10- to 14-day-old (sexually mature) females (FIG. 1(a)). This compound was 9-methyl pentacosane (9-Me-$C_{25}$) located by specific ion scanning and identified by EI mass spectrometry (FIG. 1(c). The chromatograms appear identical at first sight because, under the conditions used, the 13-, 11-, and 9-Me-$C_{25}$ isomers do not separate (FIG. 1(a), peak #8) and the latter was, there-fore, cryptically hidden (cf. FIG. 1(b)). The compound was observed exclusively in sexually mature females in SPME samples obtained from three cohorts of immature and mature male and female EAB and was therefore considered a potential contact sex pheromone for EAB. It was estimated to be present on the elytra at ca. 5-10 μg/female. (This estimate was obtained by reapplying 1.0 μl hexane solutions of 9-Me-$C_{25}$ onto freeze-killed rinsed females from hexane solutions at 0.1, 1.0 and 10.0 μg/ul and determining and comparing peak areas by resampling with SPME and GC/MS analysis as before.)
Observations and Field Bioassays Over 100 males were observed to land and make contact with dummy females during the field bioassay. Most males were observed to arrive in the "paratrooper" manner (Lelito et al. 2007[5]), flying in suddenly and landing in precise orientation on the pinned female. However, several males landed on adjacent leaves or on a different location on the same leaf as the female and spent several minutes walking around the foliage before they aligned themselves along the length of the pinned female and attempted copulation. When departing, some males immediately flew away from the female, whereas others walked onto the leaf and proceeded to feed along the edge of the leaf for several minutes before flying away. Some males were individually recognizable due to characteristic marks on their elytra, and we observed the same male make contact with several different dummy females at different times during the observation periods.

Figure 2:
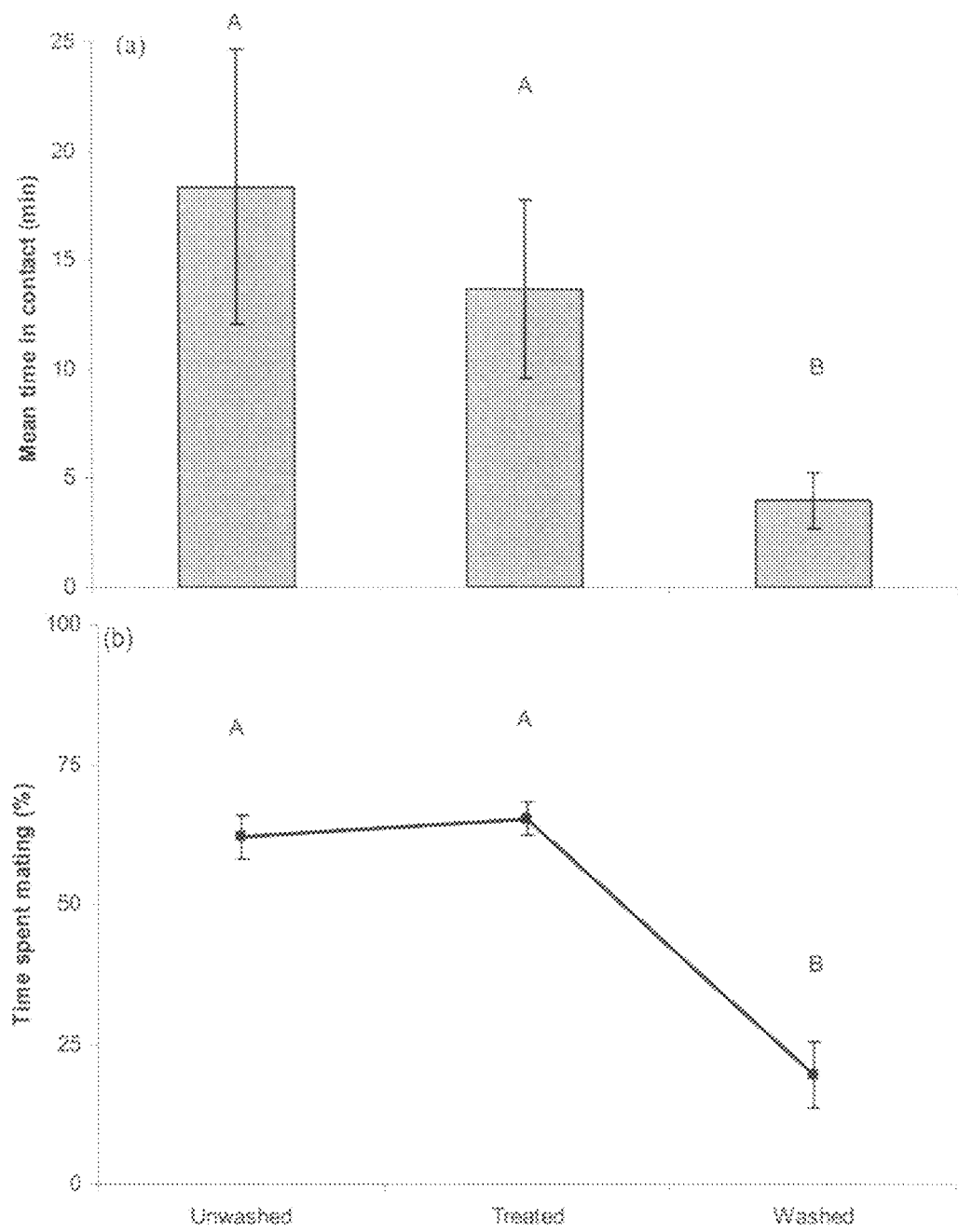
FIG. 2. Are graphs illustrating the effect of contact times, wherein (a) Bars denote the mean (±SE) number of minutes that feral EAB males spent in contact with dummy females of three different treatments: unwashed females with cuticular hydrocarbons intact (n=36 observations); treated females with cuticular hydrocarbons rinsed off with hexane then treated with putative synthetic contact pheromone (n=27 observations); and washed females that had been rinsed in hexane to remove cuticular hydrocarbons (n=43 observations). (b) Points denote the mean (±SE) percentage of total contact time that a subset of feral males spent attempting to copulate with unwashed females (n=7 observations), 9-Me-C25-treated females (n=7 observations), and washed females (n=10 observations). Means with different letters differed significantly (Kruskal-Wallis one-way ANOVA on ranks and Dunn's multiple comparison test (P<0.05).

Similar numbers of wild males landed on females of the three different treatments, with 36 landing on unwashed females, 27 on treated females, and 43 on washed females ($\chi^2$=1.809, df=2, P=0.405). Feral males spent the most time in contact with unwashed females and treated females, and the least time on washed females (F=11.7, df=2, 105, P<0.001) (FIG. 2a). The time that males spent on females treated with 9-Me-$C_{25}$ was significantly longer than that spent on washed females (t=3.817, P=0.00004) and slightly, but not significantly, less than the time spent on unwashed females (t=0.138, P=0.89) (FIG. 2). In addition, males spent approximately 60%-70% of their time attempting to mate with unwashed and 9-Me-$C_{25}$-treated females compared with only about 20% of time spent attempting to mate with washed females (F=29.349, df=2, 21, P<0.001) (FIG. 2b).
Discussion The use of cuticular hydrocarbons for mate recognition has been shown in many insect genera but little is known about the chemical ecology and reproductive behavior of buprestids. Here, we provide evidence for contact pheromones on the cuticle of female emerald ash borers that signal mate recognition and elicit copulatory behavior in feral males and we identify 9-methyl pentacosane (9-Me-$C_{25}$) as a contact pheromone—the first contact pheromone chemically identified in the Buprestidae family. This discovery improves our understanding of the chemical ecology of the EAB and other buprestids and may have potential applications for survey and management of this invasive species.

Our observations that males remained in contact much longer with unwashed than hexane-washed dead female EAB indicate the presence of contact pheromones on the female cuticle and support earlier observations by (Lelito et al. 2007[5]). Analysis of EAB cuticular hydrocarbons revealed nearly identical chemical profiles in males and females, except for one compound, 9-Me-$C_{25}$, that was present only in females that were sexually mature. Reapplication of synthetic 9-Me-$C_{25}$ to hexane-rinsed females restored almost all contact and copulatory activity in field bioassays, i.e., the time feral males spent in contact with treated females and the percentage of that time spent in attempted copulation was significantly greater than that observed with hexane-washed females and not significantly different from that observed with unwashed females. These data support the hypothesis that 9-Me-$C_{25}$ is a contact pheromone that triggers mate recognition and copulatory behavior in EAB.

Our results also confirm previous reports on the importance of visual cues in mate location. We observed feral EAB males landing in similar numbers on dead females from the three different treatments. The slightly higher number of male EAB landing on washed females in our study may be related to the short period of time that males stayed in contact with females of this treatment group; males often stayed in contact with unwashed or treated females for 30 min or more during any given observation period, making these treatments relatively less available to other males. Tactile cues may also be used by male EAB because they immediately aligned themselves with the female's body upon contact and some males remained in contact for a number of minutes even with washed females.

The paratrooper copulation behavior of male EAB was the most frequently observed mode of contact, but we also observed males landing either on the same leaf as the pinned females or on adjacent leaves and walking around for several minutes before contacting the female and attempting to mate. This behavior suggests that the visual cue provided by a resting female to a male in flight is an important one, but perhaps is not used exclusively by males to detect females.

One major difference between our results and those of (Lelito et al. 2007[5]) is the length of time males spent in contact with females. (Lelito et al. 2007[5]) reported that males spent about 4 min on unwashed females and <30 s on average with washed females, whereas we recorded contacts at least five times as long for the same treatments. The reason for this is unclear. It is possible that our hexane washes did not remove 100% of the cuticular hydrocarbons; we rinsed each female three times in n-hexane for about 2 min, whereas (Lelito et al. 2007[5]) rinsed their EAB twice in dichloromethane for 10 min each. Despite the shorter washing time used in our study, it is known that hexane readily dissolves hydrocarbons of this nature, thus effectively removing them from the female's cuticle. Regardless, the washing in hexane definitely removed an important chemical cue, as clearly evidenced by the shorter periods of time males spent in contact with such females.

The fact that feral male EAB spent a considerable amount of time in contact with the unwashed and treated females supports the use of freeze-killed EAB females as an effective technique for observing EAB mate location and mating behavior. Regardless, using freeze-killed females removes any such additional behavioral or olfactory cues that may be produced by living females, reducing confounding influences. Hence, any changes in male response in our experiment were strictly due to the washing and reapplication treatments.

The appearance of 9-Me-$C_{25}$ on only the cuticle of 10- to 14-day-old females suggests its presence may be associated with sexual maturation or, more specifically, vitellogenesis (egg maturation) in the EAB.

Biosynthesis of methyl-branched hydrocarbons such as 9-Me-$C_{25}$ likely occurs through elongation of fatty acid CoAs, with the methyl branch arising from methyl malonyl CoA in place of malonyl CoA at a specific point during chain elongation (Nelson and Blomquist 1995[12]). Little is known, however, about the stereochemistry of methyl branches, and this requires investigation because contact chemoreception may have important chiral specificity. 9-Me-$C_{25}$ has a chiral carbon, but current technology does not allow separation of the two possible enantiomers. The EAB males responded to the racemic synthetic 9-Me-$C_{25}$ compound in our field trials, but it is possible that only one enantiomer is present on the unwashed EAB female cuticle and that males respond only to that enantiomer. If so, that may explain the slightly lower contact time and copulatory response to females treated with one female equivalent of racemic 9-Me-$C_{25}$; each enantiomer would be present at only half the concentration of that on an unwashed female if only one enantiomer is naturally present.

Further work should include optimization of application rate of the contact pheromone and testing of each enantiomer vs. the racemic blend. Other orientation mechanisms that need further exploration include potential long-range pheromones that may attract beetles (Bartell et al. 2007), attractive host volatiles (Rodriguez-Saona et al. 2006; Crook et al. 2008; de Groot et al. 2008), and other visual and chemical cues (Pureswaran and Poland 2008) used in mate location, particularly in combination with the active compounds. All these mechanisms have potential for developing improved detection survey and management tools for this damaging invasive species.

TABLE 1

GC/MS analysis of cuticular hydrocarbons of mature male and female *Agrilus planipennis* sampled using solid-phase microextraction (SPME)

| Peak number | Hyrdrocarbon | Percentage of total Hydrocarbons (composite[a]) | | Diagnostic ions (EI) |
|---|---|---|---|---|
| | | Male | Female | |
| 1 | n-hexadecanoic acid | 3.3 | 5.1 | 129; 256 (M+) |
| 2 | oleic acid | 9.3 | 11.8 | [b] |
| 3 | n-$C_{23}$ | 3.9 | 2.9 | 324 (M+) |
| 4 | 11-Me-$C_{23}$ | 8.4 | 4.7 | 168/169; 196/197; 338 (M+) |
| 5 | Trace 9-Me-$C_{23}$ | <0.01 | <0.01 | 140/141; 224/225; 323 (M-15) |
| 6 | Trace 3-Me-$C_{23}$ | nd | Trace | 309 (M-29) |
| 7 | n-$C_{24}$ | 0.8 | 0.8 | 338 (M+) |
| 8 | 11,12-dimethy-$C_{23}$ | 3.2 | 2.2 | 168; 182; 196; 210 |
| 9 | n-$C_{25}$ | 8.9 | 7.8 | 352 (M+) |
| 10 | Composite | | | |
| | LHS 13-Me-$C_{25}$ | 25.0 | 15.0 | 196/197; 351 (M-15) |
| | MID 11-Me-$C_{25}$ | 17.0 | 10.0 | 168/169; 224/225; 351 (M-15) |
| | RHS 9-Me-$C_{25}$ | nd | 5.7 | 140/141; 252/253; 351 (M-15) |
| 11 | Unknown alkane | 1.9 | 1.7 | — |
| 12 | Unknown methylalkane | 1.0 | 0.7 | — |
| 13 | Unknown dimethylalkane | 2.0 | 1.9 | — |
| 14 | n-$C_{27}$ | 5.2 | 5.1 | 380 (M+) |
| 15 | 13-Me-$C_{27}$ | 7.9 | 7.6 | 196/197; 224/225; 379 (M-15) |
| 16 | Squalene | 1.2 | 3.7 | [b] |
| 17 | n-$C_{29}$ | 1.0 | 1.2 | 408 (M+) |
| 18 | 13-Me-$C_{29}$ | 1.0 | 1.8 | 196/197; 252/253 |

[a]Percentage represents an estimate from a composite sample of each sex (n = 6/composite)
[b]Library match;
nd = not detected Synthesis of Pure (S)-9-Methylpentacosane (9-Me$C_{25}$), and (R)-9-Methylpentacosane Synthesis of pure 9R- and 9S-enantiomers of 9-Me-$C_{25}$ has now been done. Based upon (soon to be published) research done by the inventors on the 11R- and 11S-isomers ie 11-Me-$C_{25}$, in respect of the related brown Spruce Longhorn Beetle (BSLB) and the demonstrated activity of the pure 11S-enantiomer as a contact sex pheromone therein, it is expected that the pure 9S-enantiomer would exhibit activity as a contact sex pheromone in the Emerald Ash Borer.

(S)-9-Methylpentacosane 1 was synthesized using (R)-citronellyl bromide 2 as the commercially available chiral synthon. This was alkylated with the Grignard reagent n-hexylmagnesium bromide 3 (prepared in situ from n-hexyl bromide and magnesium) using lithium tetrachlorocuprate as the catalyst to give alkene 4. Ozonolysis of 4 followed by reductive workup with triphenylphosphine cleaved the carbon-carbon double bond of 4 and replaced the isopropylidene group of 4 with an oxygen to give 5. A Wittig reaction with tridecyltriphenylphosphonium bromide 6 (which was prepared from tridecyl bromide and triphenylphosphine) and n-butyllithium gave a mixture of cis and trans alkenes 7, and both of these were converted to (S)-9-methylpentacosane 1 by hydrogenation with a palladium catalyst.

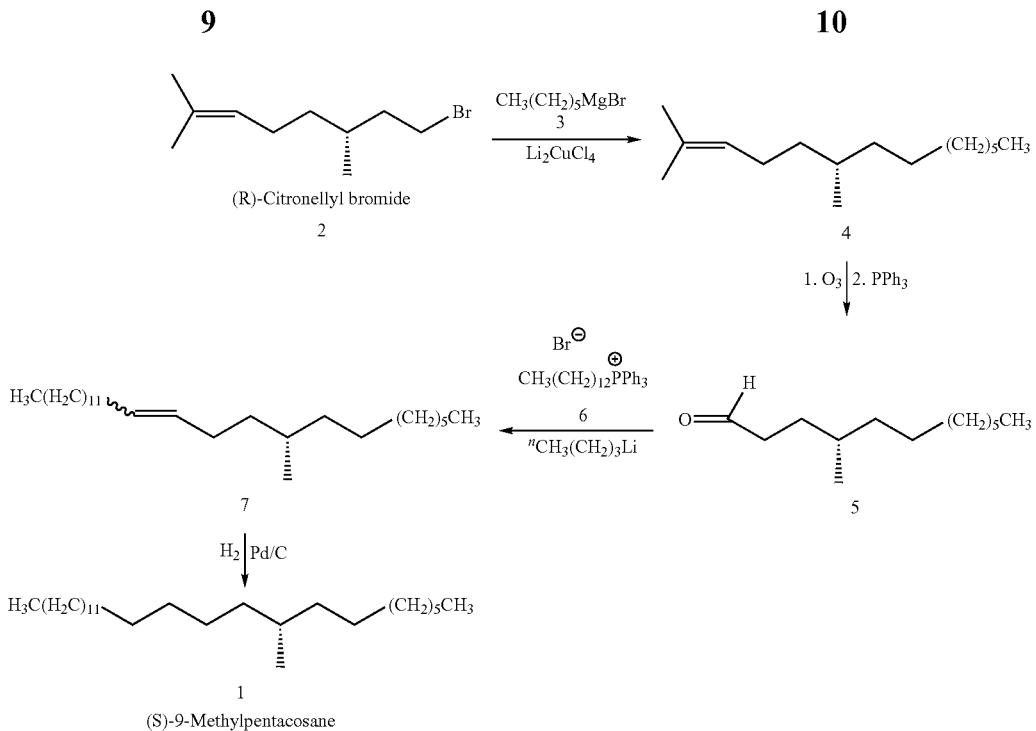
(R)-9-Methylpentacosane 8 was synthesized in exactly the same way as the (S)-enantiomer 1, except (S)-citronellyl bromide 9 was used as the starting material. Aldrich was the source of all commercially available chemicals used.
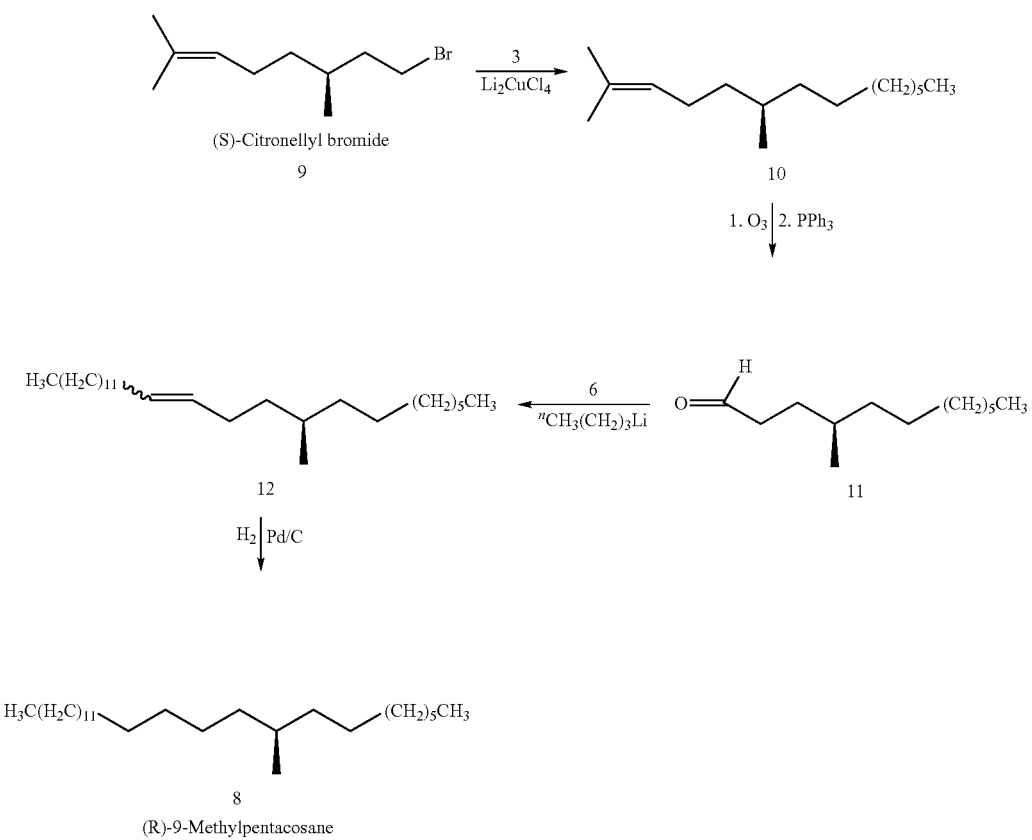

REFERENCES

1. Ginzel M D, Blomquist G J, Millar J G, Hanks L M (2003b) Role of contact pheromones in mate recognition in *Xylotrechus colonus*. J Chem Ecol 29:533-545
2. Haack R A, Jendek E, Liu K, Marchant T R, Petrice T R, Poland T M, Ye H (2002) The emerald ash borer: a new exotic pest in North America. Newslett Mich Entomol Soc 47:1-5
3. Otis G W, Youngs M E, Umphrey G (2005) Effects of colored objects and purple background on emerald ash borer trapping. In: Mastro V, Reardon R (eds) Emerald Ash Borer Research and Technology Development Meeting. USDA, Forest Health Technology Enterprise Team, Morgantown, W. Va., pp 31-32
4. Rodriguez-Saona, C, Poland T M, Miller J R, Stelinski L L, Grant G G, de Groot P, Buchan L, MacDonald L (2006) Behavioural and electrophysiological responses of the emerald ash borer, *Agrilus planipennis*, to induced volatiles of Manchurian Ash, *Fraxinus mandshurica*. Chemoecology 16:75-86
5. Lelito J P, Frazer I, Mastro V, Tumlinson J H, Boroczky K, Baker T C (2007) Visually mediated 'paratrooper copulations' in the mating behaviour of *Agrilus planipennis* (Coleoptera: Buprestidae), a highly destructive invasive pest of North American ash trees. J Insect Behav 20:537-552
6. Lelito J P, Frazer I, Mastro V, Tumlinson J H, Baker T C (2008) Novel visual-cue-based sticky traps for monitoring of emerald ash borers, *Agrilus planipennis*, J Appl Entomol 132:668-674
7. Francese J A, Mastro V C, Oliver J B, Lance D R, Youseff N, Lavalee S G (2005) Evaluation of colors for trapping *Agrilus planipennis* (Coleoptera: Buprestidae). J Entomol Sci 40:93-95
8. Crook D J, Krimian A, Francese J, Fraser I, Poland T M, Sawyer A J, Mastro V (2008) Development of a host-based semiochemical lure for trapping emerald ash borer *Agrilus planipennis* (Coleoptera: Buprestidae). Environ Entomol 37:356-365
9. de Groot P, Grant G G, Poland T M, Scharbach R, Buchan L, Nott R W, Macdonald L, Pitt D (2008) Electrophysiological response and attraction of emerald ash borer to green leaf volatiles (GLVs) emitted by host foliage. J Chem Ecol 34:1170-1179
10. Bartelt R, Cosse A A, Zilkowski B W, Fraser I (2007) Antennally active macrolide from the emerald ash borer *Agrilus planipennis* emitted predominantly by females. J Chem Ecol 33:1299-1302
11. Dunn J P, Potter D A (1988) Evidence for sexual attraction by the twolined chestnut borer, *Agrilus bilineatus* (Weber) (Coleoptera: Buprestidae). Can Entomol 120:1037-1039
12. Nelson D R, Blomquist G J (1995) Insect waxes. In: Hamilton R J (ed) Waxes: chemistry, molecular biology and functions. Oily Press, Dundee, Scotland, pp 1-90

The invention claimed is:

1. A composition for the attraction and detection of a sexually mature male Emerald Ash Borer (EAB) *Agrilus planipennis* Fairmaire (Coleoptra: Buprestidae), comprising a dead female Emerald Ash Borer as substrate and applied to the substrate, an attracting effective amount of 9-methyl pentacosane, wherein the 9-methyl pentacosane, is in a pure S-enantiomer form, and additionally comprising host plant volatiles selected from sesquiterpenes found in ash bark and ash leaf volatiles.

2. A method for the attraction and detection of a sexually mature male Emerald Ash Borer *Agrilus planipennis* (Coleoptra: Buprestidae), comprising applying to a dead female Emerald Ash Borer located in an insect habitat, an attracting effective amount of 9-methyl pentacosane and host plant volatiles selected from sesquiterpenes found in ash bark and ash leaf volatiles.

3. A method according to claim 2, wherein the 9-methyl pentacosane is in the racemic form, including its two S- and R-chiral enantiomers.

4. A method according to claim 2, wherein the 9-methyl pentacosane, is in a pure S-enantiomer form.

* * * * *